United States Patent
Miyata et al.

(10) Patent No.: US 6,723,860 B2
(45) Date of Patent: Apr. 20, 2004

(54) 7A-ALKOXY-4H-PYRANO[3,2-D]-OXAZOL-2 (3H)-ONE AND PROCESS FOR PRODUCING THE SAME

(75) Inventors: Hiroyuki Miyata, Ube (JP); Takashi Honma, Ube (JP); Yasuhito Yamamoto, Ube (JP); Kikuo Ataka, Ube (JP)

(73) Assignee: UBE Industries, Ltd., Yamaguchi (JP)

( * ) Notice: Subject to any disclaimer, the term of this patent is extended or adjusted under 35 U.S.C. 154(b) by 0 days.

(21) Appl. No.: 09/988,042

(22) Filed: Nov. 16, 2001

(65) Prior Publication Data
US 2002/0072612 A1 Jun. 13, 2002

(30) Foreign Application Priority Data
Nov. 16, 2000 (JP) ........................................ 2000-349456

(51) Int. Cl.[7] ............................................. C07D 495/04
(52) U.S. Cl. ......................................................... 549/396
(58) Field of Search ........................................... 549/396

(56) References Cited
FOREIGN PATENT DOCUMENTS

EP 0 618 926 B1 * 3/2000
EP 1 000 937 A1 * 5/2000

* cited by examiner

*Primary Examiner*—Robert W. Ramsuer
*Assistant Examiner*—Rebecca Anderson
(74) *Attorney, Agent, or Firm*—Birch, Stewart, Kolasch & Birch, LLP

(57) ABSTRACT

The present invention provides a novel 7a-alkoxy-4H-pyrano-[3,2-d]-oxazol-2(3H)-one represented by the formula (I):

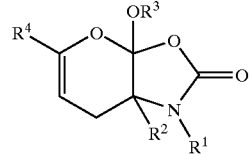

wherein $R^1$ and $R^2$ each represent a hydrogen atom, an alkyl group, an alkenyl group, an aryl group or an aralkyl group; $R^3$ represents an alkyl group, a cyclo-alkyl group, an alkenyl group, an aryl group or an aralkyl group, provided that a 2-alkenyl group is excluded from the alkenyl group of $R^3$; and $R^4$ represents an alkyl group, an aryl group, an alkoxycarbonyl group or a cyano group, and a process for producing the same which comprises reacting 5-alkoxy-2(3H)-oxazolone with an α,β-unsaturated ketone in the presence of a Lewis acid in a solvent.

9 Claims, No Drawings

7A-ALKOXY-4H-PYRANO[3,2-D]-OXAZOL-2(3H)-ONE AND PROCESS FOR PRODUCING THE SAME

BACKGROUND OF THE INVENTION

1. Field of the Invention

This invention relates to a novel 7a-alkoxy-4H-pyrano[3,2-d]-oxazol-2(3H)-one that can be used as a starting material or an intermediate for synthesizing a pharmaceutical product or an agricultural chemical and as a starting material for synthesizing other fine chemical products, and a process for producing the same. 3-Diphenylmethyl-7a-methoxy-6-methyl-4H-pyrano[3,2-d]-oxazol-2(3H)-one obtainable by the present invention can be led to 5-methylproline methyl ester that is useful as a starting material or an intermediate for synthesis of pharmaceutical products or agricultural chemicals, for example, by reacting it with trifluoroacetic acid in methylene chloride, and subsequently reacting with hydrogen in the presence of a Pd/C catalyst (as later described in Reference Example 1).

2. Prior Art

It has been conventionally known a method for producing 4-alkoxycarbonyl-2-oxazolidinone by reacting 5-alkoxy-2(3H)-oxazolones with aldehydes in an organic solvent in the presence of a Lewis acid (WO 99/02508). However, there has been known at all neither a process in which a 5-alkoxy-2(3H)-oxazolone is reacted with an α,β-unsaturated ketone in an organic solvent in the presence of a Lewis acid, nor 7a-alkoxy-4H-pyrano[3,2-d]-oxazol-2(3H)-one obtainable by the process.

That is, an object of the present invention is to provide a novel 7a-alkoxy-4H-pyrano[3,2-d]-oxazol-2(3H)-one that is useful as a starting material for synthesis of pharmaceutical products or agricultural chemicals, and for synthesis of other fine chemicals, and also to provide a process for producing the same.

SUMMARY OF THE INVENTION

The present invention relates to a 7a-alkoxy-4H-pyrano[3,2-d]-oxazol-2(3H)-one represented by the formula (I):

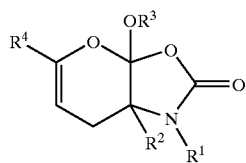

(I)

wherein $R^1$ represents a hydrogen atom, an alkyl group, an alkenyl group, an aryl group or an aralkyl group; $R^2$ represents a hydrogen atom, an alkyl group, an alkenyl group, an aryl group or an aralkyl group; $R^3$ represents an alkyl group, a cycloalkyl group, an alkenyl group, an aryl group or an aralkyl group, provided that a 2-alkenyl group is excluded from the alkenyl group of $R^3$; and $R^4$ represents an alkyl group, an aryl group, an alkoxycarbonyl group or a cyano group.

The present invention also relates to a process for producing a 7a-alkoxy-4H-pyrano[3,2-d]-oxazol-2(3H)-one represented by the formula (I):

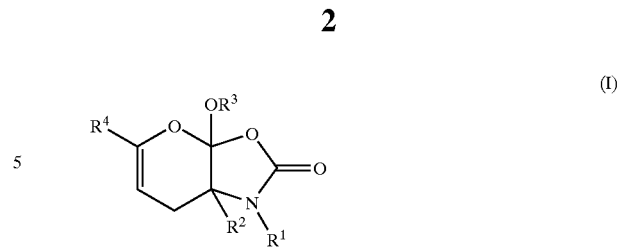

(I)

wherein $R^1$, $R^2$, $R^3$ and $R^4$ are the same as defined above, which comprises reacting a 5-alkoxy-2(3H)-oxazolone represented by the formula (II):

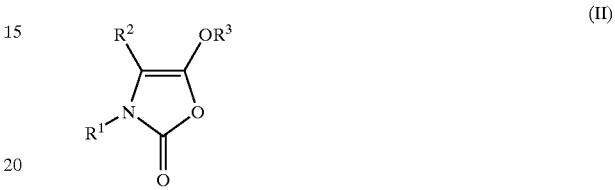

(II)

wherein $R^1$, $R^2$ and $R^3$ are the same as defined above, with an α, β-unsaturated ketone represented by the formula (III):

(III)

wherein $R^4$ is the same as defined above, in an organic solvent in the presence of a Lewis acid.

DESCRIPTION OF THE PREFERRED EMBODIMENTS

In the following, the embodiments of the present invention are explained in detail.

The 7a-alkoxy-4H-pyrano[3,2-d]-oxazol-2(3H)-one of the present invention is represented by the formula (I) and may be referred to as a compound (I) hereinafter.

An alkyl group represented by $R^1$ in the compound (1) is a straight, branched or cyclic alkyl group, example of which include a straight, branched or cyclic alkyl group having 1 to 10 carbon atoms such as methyl, ethyl, propyl (including an isomer), butyl (including each isomer), pentyl (including each isomer), hexyl (including each isomer), heptyl (including each isomer), octyl (including each isomer), nonyl (including each isomer), decyl (including each isomer), cyclopropyl, cyclobutyl, cyclopentyl, cyclohexyl, cycloheptyl, cyclooctyl, cyclononyl, cyclodecyl and menthyl groups. Preferably, they are straight, branched or cyclic alkyl groups having 1 to 6 carbon atoms, and more preferably, they are each group of methyl, ethyl, n-propyl, isopropyl, n-butyl, isobutyl, sec-butyl, tert-butyl, cyclopropyl, cyclobutyl, cyclopentyl and cyclohexyl.

An alkenyl group represented by $R^1$ in the compound (I) is a straight, branched or cyclic alkenyl group, example of which include a straight, branched or cyclic alkenyl group having 2 to 10 carbon atoms such as vinyl, propenyl (including an isomer), butenyl (including each isomer), pentenyl (including each isomer), hexenyl (including each isomer), heptenyl (including each isomer), octenyl (including each isomer), nonenyl (including each isomer), decenyl (including each isomer) groups, etc. Preferred are straight, branched or cyclic alkenyl groups having 2 to 6 carbon atoms, and more preferred are vinyl, propenyl, 1-butenyl, 2-butenyl, 1-pentenyl, 2-pentenyl, 3-pentenyl, cyclopentenyl and cyclohexenyl groups.

An aryl group represented by $R^1$ in the compound (1) is either (1) an aryl group having no substituent or (2) an aryl group having one or more substituents.

As the above-mentioned (1) aryl group having no substituent, there are exemplified by each group of phenyl, naphthyl, anthracenyl, phenanthryl, etc. Among them, preferred is each group of phenyl and naphthyl, and more preferred is a phenyl group.

As an aryl group of the above-mentioned (2) aryl group having one or more substituents, it means the same as defined for the aryl group of (1) the aryl group having no substituent. Preferred is each group of phenyl and naphthyl, and more preferred is a phenyl group.

As a substituent for (2) the aryl group having one or more substituents, there are exemplified a straight or branched alkyl group having 1 to 6 carbon atoms such as methyl, ethyl, n-propyl, isopropyl, butyl (including each isomer), pentyl (including each isomer), hexyl (including each isomer) groups, etc.; each group of hydroxyl; nitro; cyano; a halogen atom (fluorine, chlorine, bromine and iodine atoms); a straight or branched alkoxy group having 1 to 6 carbon atoms such as methoxy, ethoxy, propoxy (including each isomer), butoxy (including each isomer), pentyloxy (including each isomer), hexyloxy (including each isomer) groups, etc.; an amino group which may be substituted by a straight or branched alkyl group having 1 to 6 carbon atoms such as methyl, ethyl, propyl groups, etc.; an aralkyloxy group such as a benzyloxy group, etc.; a trimethylsilyloxy group; etc. Preferred are an alkyl group having 1 to 6 carbon atoms, an alkoxy group having 1 to 6 carbon atoms, a nitro, cyano, halogen atom, an aralkyloxy and trimethylsilyloxy group, and more preferred are methyl, ethyl, n-propyl, isopropyl, n-butyl, tert-butyl, methoxy, ethoxy, and tert-butoxy groups, fluorine, chlorine and bromine atoms, nitro and benzyloxy groups. These substituents are not limited in numbers or positions and a plural number of substituents which may be the same or different may substitute.

An aralkyl group represented by $R^1$ in the compound (1) is either (3) an aralkyl group having no substituent or (4) an aralkyl group having one or more substituents.

As the above-mentioned (3) aralkyl group having no substituent, examples may include each group of benzyl, 1-phenylethyl, 2-phenylethyl, 1-phenylpropyl, 3-phenylpropyl, 1-(1-naphthyl)ethyl, 1-naphthylmethyl, 1-(2-naphthyl)ethyl, etc. Preferred examples may include each group of benzyl, 1-phenylethyl, 2-phenylethyl, 1-(1-naphthyl)ethyl, 1-(2-naphthyl)ethyl, 1-naphthylmethyl, 1-phenylpropyl, diphenylmethyl and trityl. And more preferred are each group of benzyl, 1-phenylethyl, 1-(1-naphthyl)ethyl, 1-naphthylmethyl and diphenylmethyl.

An aralkyl group of the above-mentioned (4) aralkyl group having one or more substituents has the same meanings as defined for the aralkyl group of (3) the aralkyl group having no substituent. Preferred examples may include each group of benzyl, 1-phenylethyl, 2-phenylethyl, 1-(1-naphthyl)ethyl, 1-(2-naphthyl)ethyl, 1-naphthylmethyl, 1-phenylpropyl and diphenylmethyl. And more preferred are each group of benzyl, 1-phenylethyl, 1-(1-naphthyl)ethyl, 1-naphthylmethyl and diphenylmethyl.

A substituent for (4) the aralkyl group having one or more substituents may include a straight or branched alkyl group having 1 to 6 carbon atoms such as methyl, ethyl, n-propyl, isopropyl, butyl (including each isomer), pentyl (including each isomer), hexyl (including each isomer) groups, etc.; each group of hydroxyl; nitro; cyano; a halogen atom (fluorine, chlorine, bromine and iodine atoms); a straight or branched alkoxy group having 1 to 6 carbon atoms such as methoxy, ethoxy, propoxy (including each isomer), butoxy (including each isomer), pentyloxy (including each isomer), hexyloxy (including each isomer) groups, etc.; an amino group which may be substituted by a straight or branched alkyl group having 1 to 6 carbon atoms such as methyl, ethyl, propyl groups, etc.; an aralkyloxy group such as a benzyloxy group, etc.; a trimethylsilyloxy group; etc. Preferred are an alkyl group having 1 to 6 carbon atoms, an alkoxy group having 1 to 6 carbon atoms, a halogen atom, each group of cyano, nitro, aralkyloxy and trimethylsilyloxy, and more preferred are each group of methyl, ethyl, n-propyl, isopropyl, n-butyl, tert-butyl, methoxy, ethoxy and tert-butoxy groups, fluorine, chlorine and bromine atoms, nitro and benzyloxy groups. These substituents are not limited in numbers or positions and a plural number of substituents which may be the same or different may substitute.

Specific examples of $R^1$ in the compound (I) may include a hydrogen atom, each group of methyl, ethyl, n-propyl, isopropyl, a n-butyl, isobutyl, sec-butyl, tert-butyl, n-pentyl, n-hexyl, cyclopropyl, cyclobutyl, cyclopentyl, cyclohexyl, vinyl, propenyl, butenyl, pentenyl, hexenyl, phenyl, 2-nitrophenyl, 4-nitrophenyl, 2-cyanophenyl, 4-cyanophenyl, 3,4-dibenzyloxyphenyl, 4-benzyloxyphenyl, 2-benzyloxyphenyl, 2-chlorophenyl, 3-chlorophenyl, 4-chlorophenyl, 3,4-dichlorophenyl, 2-fluorophenyl, 3-fluorophenyl, 4-fluorophenyl, 3,4-difluorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 4-isopropylphenyl, 4-tert-butylphenyl, 2,4-dimethylphenyl, 3,4-dimethylphenyl, 4-ethylphenyl, 4-methoxyphenyl, 3,4-dimethoxyphenyl, 2-methoxyphenyl, 3-methoxyphenyl, 4-ethoxyphenyl, 2,4-diethoxyphenyl, benzyl, (1-naphthyl)methyl, 1-phenylethyl, 1-(1-naphthyl)ethyl, 1-(2-naphthyl)ethyl, diphenylmethyl, 1-(2-phenanthryl)ethyl, 1-(9-anthranyl)ethyl, trityl, 4-nitrobenzyl, 1-(4-nitrophenyl)-ethyl, 4-cyanobenzyl, 4-benzyloxybenzyl, 4-trimethylsilyloxybenzyl, 3,4-difluorobenzyl, 3,4-dichlorobenzyl, 2-fluorobenzyl, 4-fluorobenzyl, 1-(4-bromophenyl)ethyl, 1-(4-fluorophenyl)ethyl, 1-(4-chlorophenyl)ethyl, di(4-chlorophenyl)methyl, 4-methylbenzyl, 2-methylbenzyl, 2,4-di-methylbenzyl, 4-isopropylbenzyl, 4-tert-butylbenzyl, 2-methoxybenzyl, 3-methoxybenzyl, 4-methoxybenzyl, 3,4-dimethoxybenzyl, 2,4-dimethoxybenzyl, 2-ethoxybenzyl, 4-isopropoxybenzyl, 4-tert-butoxybenzyl, 1-(4-methoxyphenyl)-ethyl, di(4-methoxyphenyl)methyl, etc.

Preferred examples may include each group of methyl, ethyl, n-propyl, isopropyl, n-butyl, isobutyl, sec-butyl, tert-butyl, cyclopropyl, cyclobutyl, cyclopentyl, cyclohexyl, vinyl, propenyl, butenyl, phenyl, 2-nitrophenyl, 4-nitrophenyl, 3,4-dibenzyloxyphenyl, 4-benzyloxyphenyl, 2-chlorophenyl, 3-chlorophenyl, 4-chlorophenyl, 3,4-dichlorophenyl, 2-fluorophenyl, 3-fluorophenyl, 4-fluorophenyl, 3,4-di-fluorophenyl, 2-methylphenyl, 4-methylphenyl, 4-tert-butylphenyl, 2,4-dimethylphenyl, 3,4-dimethylphenyl, 4-ethylphenyl, 4-methoxyphenyl, 3,4-dimethoxyphenyl, 2-methoxyphenyl, 3-methoxyphenyl, benzyl, (1-naphthyl)methyl, 1-phenylethyl, 1-(1-naphthyl)ethyl, 1-(2-naphthyl)ethyl, diphenylmethyl, 4-nitrobenzyl, 1-(4-nitrophenyl)ethyl, 4-benzyloxybenzyl, 4-trimethylsilyloxybenzyl, 3,4-dichlorobenzyl, 2-fluorobenzyl, 4-fluorobenzyl, 1-(4-chlorophenyl)-ethyl, di(4-chlorophenyl)methyl, 4-methylbenzyl, 2-methylbenzyl, 2,4-dimethylbenzyl, 2-methoxybenzyl, 3-methoxybenzyl, 4-methoxybenzyl, 3,4-dimethoxybenzyl, 2,4-dimethoxybenzyl, 2-ethoxybenzyl, 1-(4-methoxyphenyl)ethyl, di(4-methoxyphenyl)methyl.

More preferred examples may include each group of methyl, ethyl, n-propyl, isopropyl, n-butyl, tert-butyl, cyclopropyl, cyclobutyl, cyclopentyl, cyclohexyl, vinyl, propenyl, butenyl, phenyl, 3,4-dibenzyloxyphenyl, 4-benzyloxyphenyl, 4-chlorophenyl, 3,4-dichlorophenyl, 4-fluorophenyl, 2-methylphenyl, 4-methylphenyl, 4-tert-butylphenyl, 2,4-dimethylphenyl, 3,4-dimethylphenyl, 4-methoxyphenyl, 3,4-dimethoxyphenyl, 2-methoxyphenyl, benzyl, (1-naphthyl)methyl, 1-phenylethyl, 1-(1-naphthyl)-ethyl, 1-(2-naphthyl)ethyl, diphenylmethyl, 4-methylbenzyl, 2,4-dimethylbenzyl, 4-methoxybenzyl, 3,4-dimethoxybenzyl, 2,4-dimethoxybenzyl, di(4-methoxyphenyl)methyl, etc.

An alkyl group represented by $R^2$ in the compound (1) may be either (5) an alkyl group having no substituent or (6) an alkyl group having one or more substituents.

The above-mentioned (5) alkyl group having no substituent may include, for example, a straight, branched or cyclic alkyl group, example of which may include a straight, branched or cyclic alkyl group having 1 to 10 carbon atoms such as methyl, ethyl, propyl (including an isomer), butyl (including each isomer), pentyl (including each isomer), hexyl (including each isomer), heptyl (including each isomer), octyl (including each isomer), nonyl (including each isomer), decyl (including each isomer), cyclopropyl, cyclobutyl, cyclopentyl, cyclohexyl, cycloheptyl, cyclooctyl, cyclononyl, cyclodecyl and menthyl groups. Preferably, they are straight, branched or cyclic alkyl groups having 1 to 6 carbon atoms, and more preferably, they are methyl, ethyl, n-propyl, isopropyl, n-butyl, isobutyl, sec-butyl, tert-butyl, cyclopropyl, cyclobutyl, cyclopentyl and cyclohexyl groups.

An alkyl group of the above-mentioned (6) alkyl group having one or more substituents has the same meanings as defined for the alkyl group of (5) the alkyl group having no substituent. Preferred is a straight, branched or cyclic alkyl group having 1 to 6 carbon atoms, and more preferred are each group of methyl, ethyl, n-propyl, isopropyl, n-butyl, isobutyl, sec-butyl, tert-butyl, cyclopropyl, cyclobutyl, cyclopentyl and cyclohexyl.

As a substituent for (6) the alkyl group having one or more substituents, examples may include each group of hydroxy; methoxy; benzyloxy; trimethylsilyloxy; tert-butyldimethylsilyloxy; acetoxy; thiomethyl; indolyl; imidazolyl; acylamino; methoxycarbonyl; ethoxycarbonyl; tert-butyloxycarbonyl; benzyloxycarbonyl; guanidyl; mercapto; amino; tert-butoxycarbonylamino; benzyloxycarbonylamino; methoxycarbonylamino; ethoxycarbonylamino; aminocarbonyl, etc. Preferred is each group of methoxy, benzyloxy, tert-butyl-dimethylsilyloxy, acetoxy, thiomethyl, indolyl, imidazolyl, acylamino, methoxycarbonyl, tert-butoxycarbonylamino and benzyloxycarbonylamino group. More prefer-ably, they are each group of benzyloxy, tert-butyldimethylsilyloxy, acetoxy, thiomethyl, indolyl, imidazolyl, methoxycarbonyl, and tert-butoxycarbonylamino. These substituents are not limited in numbers or positions and a plural number of substituents which may be the same or different may substitute.

An alkenyl group represented by $R^2$ in the compound (I) is a straight, branched or cyclic alkenyl group, example of which may include a straight, branched or cyclic alkenyl group having 2 to 10 carbon atoms such as vinyl, propenyl (including an isomer), butenyl (including each isomer), pentenyl (including each isomer), hexenyl (including each isomer), heptenyl (including each isomer), octenyl (including each isomer), nonenyl (including each isomer), decenyl (including each isomer) groups, etc. Preferred are straight, branched or cyclic alkenyl groups having 2 to 6 carbon atoms, and more preferred is each group of vinyl, propenyl, 1-butenyl, 2-butenyl, 1-pentenyl, 2-pentenyl, 3-pentenyl, cyclopentenyl and cyclohexenyl.

An aryl group represented by $R^2$ in the compound (I) is either (7) an aryl group having no substituent or (8) an aryl group having one or more substituents.

As the above-mentioned (7) aryl group having no substituent, there are exemplified by each group of phenyl, naphthyl, anthracenyl, phenanthryl, etc. Among them, preferred is each group of phenyl and naphthyl, and more preferred is a phenyl group.

An aryl group of the above-mentioned (8) aryl group having one or more substituents has the same meanings as defined for the aryl group of (7) the aryl group having no substituent. Preferred is each group of phenyl and naphthyl, and more preferred is a phenyl group.

As a substituent for (8) the aryl group having one or more substituents, there are exemplified by a straight or branched alkyl group having 1 to 6 carbon atoms such as methyl, ethyl, n-propyl, isopropyl, butyl (including each isomer), pentyl (including each isomer), hexyl (including each isomer) groups, etc.; each group of hydroxyl; nitro; cyano; halogen atom (fluorine, chlorine, bromine and iodine atoms); a straight or branched alkoxy group having 1 to 6 carbon atoms such as methoxy, ethoxy, propoxy (including each isomer), butoxy (including each isomer), pentyloxy (including each isomer), hexyloxy (including each isomer) groups, etc.; an amino group which may be substituted by a straight or branched alkyl group having 1 to 6 carbon atoms such as methyl, ethyl, propyl groups, etc.; an aralkyloxy group such as a benzyloxy group, etc.; a trimethylsilyloxy group; etc. Preferred are an alkyl group having 1 to 6 carbon atoms, an alkoxy group having 1 to 6 carbon atoms, a halogen atom, each group of cyano, nitro, benzyloxy and trimethylsilyloxy, and more preferred are each group of methyl, ethyl, n-propyl, isopropyl, n-butyl, tert-butyl, methoxy, ethoxy, tert-butoxy, fluorine, chlorine and bromine atoms, and each group of nitro and benzyloxy.

These substituents are not limited in numbers or positions and a plural number of substituents which may be the same or different may substitute.

An aralkyl group represented by $R^2$ in the compound (1) is either (9) an aralkyl group having no substituent or (10) an aralkyl group having one or more substituents.

As the above-mentioned (9) aralkyl group having no substituent, examples may include each group of benzyl, 1-phenylethyl, 2-phenylethyl, 1-phenylpropyl, 3-phenylpropyl, 4-phenylbutyl, 1-(1-naphthyl)ethyl, 1-naphthylmethyl, 1-(2-naphthyl)ethyl, etc. Preferred examples may include each group of benzyl, 2-phenylethyl, 1-(1-naphthyl)ethyl group, a 1-(2-naphthyl)ethyl, 1-naphthylmethyl, 2-phenylpropyl, 3-phenylpropyl, 4-phenylbutyl, diphenylmethyl and trityl. And more preferred is each group of benzyl, 1-naphthylmethyl, 2-phenylethyl, 3-phenylpropyl, 4-phenylbutyl and diphenylmethyl.

An aralkyl group of the above-mentioned (10) aralkyl group having one or more substituents has the same meanings as defined for the aralkyl group of (9) the aralkyl group having no substituent. Preferred examples may include each group of benzyl, 2-phenylethyl, 1-(1-naphthyl)ethyl group, 1-(2-naphthyl)ethyl, 1-naphthylmethyl, 2-phenylpropyl, 3-phenylpropyl, 4-phenylbutyl, diphenylmethyl and trityl. More preferred is each group of benzyl, 1-naphthylmethyl, 2-phenylethyl, 3-phenypropyl, 4-phenylbutyl and diphenylmethyl.

As a substituent for (10) the aralkyl group having one or more substituents, examples may include a straight or branched alkyl group having 1 to 6 carbon atoms such as methyl, ethyl, n-propyl, isopropyl, butyl (including each isomer), pentyl (including each isomer), hexyl (including each isomer) groups, etc.; each group of hydroxyl; nitro; cyano; halogen atom (fluorine, chlorine, bromine and iodine atoms); a straight or branched alkoxy group having 1 to 6 carbon atoms such as methoxy, ethoxy, propoxy (including each isomer), butoxy (including each isomer), pentyloxy (including each isomer), hexyloxy (including each isomer) groups, etc.; an amino group which may be substituted by a straight or branched alkyl group having 1 to 6 carbon atoms such as methyl, ethyl, propyl groups, etc.; an aralkyloxy group such as a benzyloxy group, etc.; a trimethylsilyloxy group; etc. Preferred are an alkyl group having 1 to 6 carbon atoms, an alkoxy group having 1 to 6 carbon atoms, a halogen atom, and each group of cyano, nitro, benzyloxy and trimethylsilyloxy, and more preferred is each group of methyl, ethyl, n-propyl, isopropyl, n-butyl, tert-butyl, methoxy, ethoxy, tert-butoxy, fluorine, chlorine and bromine atoms, each group of nitro and benzyloxy. These substituents are not limited in numbers or positions and a plural number of substituents which may be the same or different may substitute.

Specific examples of $R^2$ in the compound (I) may include a hydrogen atom, each group of methyl, ethyl, n-propyl, isopropyl, n-butyl, isobutyl, sec-butyl, tert-butyl, n-hexyl, heptyl, octyl, nonyl, decyl, cyclopropyl, cyclobutyl, cyclopentyl, cyclohexyl, cycloheptyl, cyclooctyl, cyclononyl, cyclodecyl, methoxymethyl, benzyloxymethyl group, 1-(benzyloxy) ethyl, trimethylsilyloxymethyl, tert-butyldimethylsilyloxymethyl, acetoxymethyl, methylthiomethyl, indolylmethyl, aminocarbonylmethyl, 4-tert-butoxycarbonylaminobutyl, 4-benzyloxycarbonylaminobutyl, methoxycarbonylmethyl, 2-methoxycarbonylethyl, ethoxycarbonylmethyl, 2-methylthioethyl, imidazolylmethyl, 3-guanidylpropyl, 2-aminocarbonylethyl, hydroxymethyl, mercaptomethyl, vinyl, propenyl, 1-butenyl, 2-butenyl, 1-pentenyl, 2-pentenyl, 3-pentenyl, 1-hexenyl, 2-hexenyl, 3-hexenyl, 4-hexenyl, cyclopentenyl, cyclohexenyl, 2-heptenyl, 3-heptenyl, 4-heptenyl, 2-octenyl, 3-octenyl, 2-nonenyl, 2-decenyl, phenyl, 1-naphthyl, 2-naphthyl, anthracenyl, phenanthryl, 2-methylphenyl, 3-methylphenyl, 4-methylphenyl, 4-benzyloxyphenyl, 3-benzyloxyphenyl, 2-benzyloxyphenyl, 4-trimethylsilyloxyphenyl, 4-nitrophenyl, 2-nitrophenyl, 3-nitrophenyl, 4-cyanophenyl, 3-cyanophenyl, 2-cyanophenyl, 4-fluorophenyl, 3-fluorophenyl, 2-fluorophenyl, 4-chlorophenyl, 3-chlorophenyl, 2-chlorophenyl, 4-bromophenyl, 2-bromophenyl, 4-iodophenyl, 4-methoxyphenyl, 3-methoxyphenyl, 2-methoxyphenyl, 3,4-dimethoxyphenyl, 4-ethoxyphenyl, 3-methoxy-4-ethoxyphenyl, 4-tert-butoxyphenyl, 3,4-methylenedioxyphenyl, 4-ethylphenyl, 4-n-propylphenyl, 4-isopropylphenyl, 4-tert-butylphenyl, 4-dimethylaminophenyl, 4-monomethylaminophenyl, 4-diethylamionophenyl, benzyl, 1-phenylethyl, 2-phenylethyl, 1-phenylpropyl, 2-phenylpropyl, 3-phenylpropyl, 4-phenylbutyl, 1-(1-naphthyl)ethyl, 1-(2-naphthyl)ethyl, 1-naphthylmethyl, diphenylmethyl, trityl, 4-methylbenzyl, 3-methylbenzyl, 2-methylbenzyl, 4-ethylbenzyl, isobutylbenzyl, 4-isopropylbenzyl, 4-tert-butylbenzyl, 4-methoxybenzyl, 3-methoxybenzyl, 2-methoxybenzyl, 3,4-dimethoxybenzyl, 3,4-methylenedioxybenzyl, 3,4-diethoxybenzyl, 4-benzyloxybenzyl, 3-benzyloxybenzyl, 4-trimethylsilyloxybenzyl, 4-tert-butyldimethylsilyloxybenzyl, 4-nitrobenzyl, 3-nitrobenzyl, 2-nitrobenzyl, 4-fluorobenzyl, 3-fluorobenzyl, 2-fluorobenzyl, 4-chlorobenzyl, 3-chlorobenzyl, 2-chlorobenzyl, 4-bromobenzyl, 4-iodobenzyl, 4-cyanobenzyl, 4-dimethylaminobenzyl, 2-(4-methoxyphenyl)ethyl, 2-(4-benzyloxyphenyl)ethyl, 2-(4-tert-butyldimethylsilyloxyphenyl)ethyl, 2-(4-nitrophenyl)ethyl, etc.

Preferred examples may include a hydrogen atom, each group of methyl, ethyl, propyl, isopropyl, n-butyl, sec-butyl, tert-butyl, n-hexyl, cyclopropyl, cyclobutyl, cyclopentyl, cyclohexyl, methoxymethyl, benzyloxymethyl, 1-(benzyloxy)-ethyl, trimethylsilyloxymethyl, tert-butyldimethylsilyl oxymethyl, acetoxymethyl, methylthiomethyl, indolylmethyl, aminocarbonylmethyl, 4-tert-butoxycarbonylaminobutyl, 4-benzyloxycarbonylaminobutyl, methoxycarbonylmethyl, 2-methoxycarbonylethyl, ethoxycarbonylmethyl, 2-(methylthio)-ethyl, imidazolylmethyl, 2-aminocarbonylethyl, hydroxymethyl, mercaptomethyl, vinyl, propenyl, 1-butenyl, 2-butenyl, 1-pentenyl, 2-pentenyl, 3-pentenyl, 1-hexenyl, 2-hexenyl, 3-hexenyl, 4-hexenyl, cyclopentenyl, cyclohexenyl, phenyl, 1-naphthyl, 2-naphthyl, 2-methylphenyl, 3-methylphenyl, 4-methylphenyl, 4-benzyloxyphenyl, 3-benzyloxyphenyl, 2-benzyloxyphenyl, 4-trimethylsilyloxyphenyl, 4-nitrophenyl, 2-nitrophenyl, 3-nitrophenyl, 4-cyanophenyl, 4-fluorophenyl, 4-chlorophenyl, 3-chlorophenyl, 4-bromophenyl, 4-iodophenyl, 4-methoxyphenyl, 3-methoxyphenyl, 3,4-dimethoxyphenyl, 4-tert-butoxyphenyl, 3,4-methylenedioxyphenyl, 4-ethylphenyl, 4-n-propylphenyl, 4-isopropylphenyl, 4-tert-butylphenyl, 4-dimethylaminophenyl, 4-diethylamionophenyl, benzyl, 1-phenylethyl, 2-phenylethyl, 1-phenylpropyl, 2-phenylpropyl, 3-phenylpropyl, 4-phenylbutyl, 1-(1-naphthyl)ethyl, 1-(2-naphthyl)ethyl, 1-naphthylmethyl, 4-methylbenzyl, 4-ethylbenzyl, 4-isobutylbenzyl, 4-isopropylbenzyl, 4-tert-butylbenzyl, 4-methoxybenzyl, 3,4-dimethoxybenzyl, 3,4-methylenedioxybenzyl, 3,4-diethoxybenzyl, 4-benzyloxybenzyl, 4-tert-butyldimethylsilyloxybenzyl, 4-nitrobenzyl, 2-nitrobenzyl, 4-fluorobenzyl, 2-fluorobenzyl, 4-chlorobenzyl, 3-chlorobenzyl, 4-bromobenzyl, 4-iodobenzyl, 4-cyanobenzyl, 4-dimethylaminobenzyl, 2-(4-methoxyphenyl)ethyl, 2-(4-benzyloxyphenyl)-ethyl, 2-(4-tert-butyldimethylsilyloxyphenyl)ethyl and 2-(4-nitrophenyl)ethyl.

More preferred examples may include a hydrogen atom, each group of methyl, ethyl, propyl, isopropyl, n-butyl, sec-butyl, tert-butyl, n-hexyl, cyclopropyl, cyclobutyl, cyclopentyl, cyclohexyl, methoxymethyl, benzyloxymethyl, 1-(benzyloxy)ethyl, tert-butyldimethylsilyloxymethyl, acetoxymethyl, methylthiomethyl, indolylmethyl, aminocarbonylmethyl, 4-tert-butoxycarbonylaminobutyl, 4-benzyloxycarbonylaminobutyl, methoxycarbonylmethyl, 2-methoxycarbonylethyl, 2-methylthioethyl, 2-aminocarbonylethyl, vinyl, propenyl, 1-butenyl, 2-butenyl, 1-pentenyl, 2-pentenyl, 3-pentenyl, 1-hexenyl, 2-hexenyl, 3-hexenyl, 4-hexenyl, cyclopentenyl, cyclohexenyl, phenyl, 1-naphthyl, 2-naphthyl, 2-methylphenyl, 3-methylphenyl, 4-methylphenyl, 4-benzyloxyphenyl, 4-trimethylsilyloxyphenyl, 4-nitrophenyl, 4-cyanophenyl, 4-fluorophenyl, 4-chlorophenyl, 4-bromophenyl, 4-iodophenyl, 4-methoxyphenyl, 3,4-dimethoxyphenyl, 4-tert-butoxyphenyl, 3,4-methylenedioxyphenyl, 4-dimethylamionophenyl, 4-diethylamionophenyl, benzyl, 1-phenylethyl, 2-phenylethyl, 1-phenylpropyl, 2-phenylpropyl, 3-phenylpropyl, 4-phenylbutyl, 1-(1-naphthyl)ethyl, 1-(2-naphthyl)ethyl, 1-naphthylmethyl, 4-methylbenzyl, 4-isobutylbenzyl, 4-isopropylbenzyl, 4-tert-butylbenzyl, 4-methoxybenzyl, 3,4-dimethoxybenzyl, 3,4-methylenedioxybenzyl, 4-benzyloxybenzyl, 4-tert-butyldimethylsilyloxybenzyl, 4-nitrobenzyl, 4-fluorobenzyl, 4-chlorobenzyl, 4-bromobenzyl, 4-iodobenzyl, 4-cyanobenzyl, 4-dimethylaminobenzyl, 2-(4-methoxyphenyl)ethyl, 2-(4-benzyloxyphenyl)-ethyl, 2-(4-tert-butyldimethylsilyloxyphenyl)ethyl and 2-(4-nitrophenyl)ethyl.

An alkyl group represented by $R^3$ in the compound (1) is a straight, branched or cyclic alkyl group, example of which may include a straight, branched or cyclic alkyl group having 1 to 10 carbon atoms such as methyl, ethyl, propyl (including an isomer), butyl (including each isomer), pentyl (including each isomer), hexyl (including each isomer), heptyl (including each isomer), octyl (including each isomer), nonyl (including each isomer), decyl (including each isomer), cyclopropyl, cyclobutyl, cyclopentyl, cyclohexyl, cycloheptyl, cyclooctyl, cyclononyl and cyclodecyl groups. Preferably, they are straight, branched or cyclic alkyl groups having 1 to 6 carbon atoms, and more preferably, they are each group of methyl, ethyl, n-propyl, isopropyl, n-butyl, isobutyl, sec-butyl, tert-butyl, cyclopropyl, cyclobutyl, cyclopentyl and cyclohexyl.

An alkenyl group represented by $R^3$ in the compound (I) is a straight, branched or cyclic alkenyl group, example of which may include a straight, branched or cyclic alkenyl group having 2 to 10 carbon atoms such as vinyl, propenyl (including an isomer), butenyl (including each isomer), pentenyl (including each isomer), hexenyl (including each isomer), heptenyl (including each isomer), octenyl (including each isomer), nonenyl (including each isomer), decenyl (including each isomer) groups, etc. Preferred are straight, branched or cyclic alkenyl groups having 2 to 6 carbon atoms, and more preferred is each group of vinyl, propenyl, 1-butenyl, 2-butenyl, 1-pentenyl, 2-pentenyl, 3-pentenyl, cyclopentenyl and cyclohexenyl.

An aryl group represented by $R^3$ in the compound (1) is either (11) an aryl group having no substituent or (12) an aryl group having one or more substituents.

As the above-mentioned (11) aryl group having no substituent, there are exemplified by each group of phenyl, naphthyl, anthracenyl, phenanthryl, etc. Among them, preferred is each group of phenyl and naphthyl, and more preferred is a phenyl group.

An aryl group of the above-mentioned (12) aryl group having one or more substituents has the same meanings as defined for the aryl group of (11) the aryl group having no substituent. Preferred is each group of phenyl and naphthyl, and more preferred is a phenyl group.

As a substituent for (12) the aryl group having one or more substituents, there are exemplified by a straight or branched alkyl group having 1 to 6 carbon atoms such as methyl, ethyl, n-propyl, isopropyl, butyl (including each isomer), pentyl (including each isomer), hexyl (including each isomer) groups, etc.; each group of hydroxyl; nitro; cyano; halogen atom (fluorine, chlorine, bromine and iodine atoms); a straight or branched alkoxy group having 1 to 6 carbon atoms such as methoxy, ethoxy, propoxy (including each isomer), butoxy (including each isomer), pentyloxy (including each isomer), hexyloxy (including each isomer) groups, etc.; an amino group which may be substituted by a straight or branched alkyl group having 1 to 6 carbon atoms such as methyl, ethyl, propyl groups, etc.; an aralkyloxy group such as a benzyloxy group, etc.; and a trimethylsilyloxy group; etc.

Preferred are an alkyl group having 1 to 6 carbon atoms, an alkoxy group having 1 to 6 carbon atoms, a halogen atom, each group of cyano, nitro, benzyloxy and trimethylsilyloxy, and more preferred is each group of methyl, ethyl, n-propyl, isopropyl, n-butyl, tert-butyl, methoxy, ethoxy, tert-butoxy, fluorine, chlorine and bromine atoms, each group of nitro and benzyloxy. These substituents are not limited in numbers or positions and a plural number of substituents which may be the same or different may substitute.

An aralkyl group represented by $R^3$ in the compound (1) is either (13) an aralkyl group having no substituent or (14) an aralkyl group having one or more substituents.

As the above-mentioned (13) aralkyl group having no substituent, examples may include each group of benzyl, 1-phenylethyl, 2-phenylethyl, 1-phenylpropyl, 2-phenylpropyl, 3-phenylpropyl, 4-phenylbutyl, 1-(1-naphthyl)ethyl, 1-naphthylmethyl, 1-(2-naphthyl)ethyl, etc. Preferred examples may include each group of benzyl, 2-phenylethyl, 1-(1-naphthyl)ethyl, 1-(2-naphthyl)ethyl, 1-naphthylmethyl, 2-phenylpropyl, 3-phenylpropyl, 4-phenylbutyl, diphenylmethyl and trityl. And more preferred is each group of benzyl, 1-naphthylmethyl, 2-phenylethyl, 3-phenylpropyl, 4-phenylbutyl and diphenylmethyl.

An aralkyl group of the above-mentioned (14) aralkyl group having one or more substituents has the same meanings as defined for the aralkyl group of (13) the aralkyl group having no substituent. Preferred examples may include each group of benzyl, 2-phenylethyl, 1-(1-naphthyl)ethyl, 1-(2-naphthyl)ethyl, 1-naphthylmethyl, 2-phenylpropyl, 3-phenylpropyl, 4-phenylbutyl, diphenylmethyl and trityl. And more preferred is each group of benzyl, 1-naphthylmethyl, 2-phenylethyl, 3-phenylpropyl, 4-phenylbutyl and diphenylmethyl.

As a substituent for (14) the aralkyl group having one or more substituents, examples may include a straight or branched alkyl group having 1 to 6 carbon atoms such as methyl, ethyl, n-propyl, isopropyl, butyl (including each isomer), pentyl (including each isomer), hexyl (including each isomer) groups, etc.; each group of hydroxyl; nitro; cyano; halogen atom (fluorine, chlorine, bromine and iodine atoms); a straight or branched alkoxy group having 1 to 6 carbon atoms such as methoxy, ethoxy, propoxy (including each isomer), butoxy (including each isomer), pentyloxy (including each isomer), hexyloxy (including each isomer) groups, etc.; an amino group which may be substituted by a straight or branched alkyl group having 1 to 6 carbon atoms such as methyl, ethyl, propyl groups, etc.; an aralkyloxy group such as a benzyloxy group, etc.; a trimethylsilyloxy group; etc.

Preferred are an alkyl group having 1 to 6 carbon atoms, an alkoxy group having 1 to 6 carbon atoms, a halogen atom, each group of cyano, nitro, benzyloxy and trimethylsilyloxy, and more preferred is each group of methyl, ethyl, n-propyl, isopropyl, n-butyl, tert-butyl, methoxy, ethoxy, tert-butoxy, fluorine, chlorine and bromine atoms, each group of nitro and benzyloxy. These substituents are not limited in numbers or positions and a plural number of substituents which may be the same or different may substitute.

Specific examples of $R^3$ in the compound (I) may include each group of methyl, ethyl, n-propyl, isopropyl, n-butyl, isobutyl, sec-butyl, tert-butyl, n-hexyl, heptyl, octyl, nonyl, decyl, cyclopropyl, cyclobutyl, cyclopentyl, cyclohexyl, cycloheptyl, cyclooctyl, cyclononyl, cyclodecyl, menthyl, 8-phenylmenthyl, vinyl, propenyl, 1-butenyl, 1-pentenyl, 3-pentenyl, 1-hexenyl, 3-hexenyl, 4-hexenyl, cyclopentenyl, cyclohexenyl, 3-heptenyl, 4-heptenyl, 3-octenyl, 3-nonenyl, 3-decenyl, phenyl, 1-naphthyl, 2-naphthyl, anthracenyl, phenanthryl, 2-methylphenyl, 3-methylphenyl, 4-methylphenyl, 4-benzyloxyphenyl, 3-benzyloxyphenyl, 2-benzyloxyphenyl, 4-trimethylsilyloxyphenyl, 4-nitrophenyl, 2-nitrophenyl, 3-nitrophenyl, 4-cyanophenyl, 3-cyanophenyl, 2-cyanophenyl, 4-fluorophenyl, 3-fluorophenyl, 2-fluorophenyl, 4-chlorophenyl, 3-chlorophenyl, 2-chlorophenyl, 4-bromophenyl, 2-bromophenyl, 4-iodophenyl, 4-methoxyphenyl, 3-methoxyphenyl, 2-methoxyphenyl, 3,4-dimethoxyphenyl, 4-ethoxyphenyl, 3-methoxy-4-ethoxyphenyl, 4-tert-butoxyphenyl, 3,4-methylenedioxyphenyl, 4-ethylphenyl, 4-n-propylphenyl, 4-isopropylphenyl, 4-tert-butylphenyl, 4-dimethylaminophenyl, 4-monomethylaminophenyl, 4-diethylamionophenyl, benzyl, 1-phenylethyl, 2-phenylethyl, 1-phenylpropyl, 2-phenylpropyl, 3-phenylpropyl, 4-phenylbutyl, 1-(1-naphthyl)ethyl, 1-(2-naphthyl)ethyl, 1-naphthylmethyl, diphenylmethyl, trityl, 4-methylbenzyl, 3-methylbenzyl, 2-methylbenzyl, 4-ethylbenzyl, 4-isobutylbenzyl, 4-isopropylbenzyl, 4-tert-butylbenzyl, 4-methoxybenzyl, 3-methoxybenzyl, 2-methoxybenzyl, 3,4-dimethoxybenzyl, 3,4-methylenedioxybenzyl, 3,4-diethoxybenzyl, 4-benzyloxybenzyl, 3-benzyloxybenzyl, 4-trimethylsilyloxybenzyl, 4-tert-butyldimethylsilyloxybenzyl, 4-nitrobenzyl, 3-nitrobenzyl, 2-nitrobenzyl, 4-fluorobenzyl, 3-fluorobenzyl, 2-fluorobenzyl, 4-chlorobenzyl, 3-chlorobenzyl, 2-chlorobenzyl, 4-bromobenzyl, 4-iodobenzyl, 4-cyanobenzyl, 4-dimethylaminobenzyl, 2-(4-methoxyphenyl)ethyl, 2-(4-benzyloxyphenyl)ethyl, 2-(4-tert-butyldimethylsilyloxyphenyl)ethyl, 2-(4-nitrophenyl)ethyl, etc.

Preferred examples may include each group of methyl, ethyl, n-propyl, isopropyl, n-butyl, sec-butyl, tert-butyl, n-hexyl, cyclopropyl, cyclobutyl, cyclopentyl, cyclohexyl group, menthyl, 8-phenylmenthyl, vinyl, propenyl, 1-butenyl, 1-pentenyl, 3-pentenyl, 1-hexenyl, 3-hexenyl, 4-hexenyl, cyclopentenyl, cyclohexenyl, phenyl, 1-naphthyl, 2-naphthyl, 2-methylphenyl, 3-methylphenyl, 4-methylphenyl, 4-benzyloxyphenyl, 3-benzyloxyphenyl, 2-benzyloxyphenyl, 4-trimethylsilyloxyphenyl, 4-nitrophenyl, 2-nitrophenyl, 3-nitrophenyl, 4-cyanophenyl, 4-fluorophenyl, 4-chlorophenyl, 3-chlorophenyl, 4-bromophenyl, 4-iodophenyl, 4-methoxyphenyl, 3-methoxyphenyl, 3,4-dimethoxyphenyl, 4-tert-butoxyphenyl, 3,4-methylenedioxyphenyl, 4-ethylphenyl, 4-(n-propyl)phenyl, 4-isopropylphenyl, 4-tert-butylphenyl, 4-dimethylaminophenyl, 4-diethylamionophenyl, benzyl, 1-phenylethyl, 2-phenylethyl, 1-phenylpropyl, 2-phenylpropyl, 3-phenylpropyl, 4-phenylbutyl, 1-(1-naphthyl)ethyl, 1-(2-naphthyl)ethyl, 1-naphthylmethyl, 4-methylbenzyl, 4-ethylbenzyl, 4-isobutylbenzyl, 4-isopropylbenzyl, 4-tert-butylbenzyl, 4-methoxybenzyl, 3,4-dimethoxybenzyl, 3,4-methylenedioxybenzyl, 3,4-diethoxybenzyl, 4-benzyloxybenzyl, 4-tert-butyldimethylsilyloxybenzyl, 4-nitrobenzyl, 2-nitrobenzyl, 4-fluorobenzyl, 2-fluorobenzyl, 4-chlorobenzyl, 3-chlorobenzyl, 4-bromobenzyl, 4-iodobenzyl, 4-cyanobenzyl, 4-dimethylaminobenzyl, 2-(4-methoxyphenyl)ethyl, 2-(4-benzyloxyphenyl)ethyl, 2-(4-tert-butyldimethylsilyloxyphenyl)ethyl, 2-(4-nitrophenyl)ethyl, etc.

More preferred examples may include each group of methyl, ethyl, n-propyl, isopropyl, n-butyl, sec-butyl, tert-butyl, n-hexyl, cyclopropyl, cyclobutyl, cyclopentyl, cyclohexyl, menthyl, 8-phenylmenthyl, vinyl, propenyl, 1-butenyl, 1-pentenyl, 3-pentenyl, 1-hexenyl, 3-hexenyl, 4-hexenyl, cyclopentenyl, cyclohexenyl, phenyl, 1-naphthyl, 2-naphthyl, 2-methylphenyl, 3-methylphenyl, 4-methylphenyl, 4-benzyloxyphenyl, 4-trimethylsilyloxyphenyl, 4-nitrophenyl, 4-cyanophenyl, 4-fluorophenyl group, a 4-chlorophenyl, 4-bromophenyl, 4-iodophenyl, 4-methoxyphenyl, 3,4-dimethoxyphenyl, 4-tert-butoxyphenyl, 3,4-methylenedioxyphenyl, 4-dimethylaminophenyl, 4-diethylamionophenyl, benzyl, 1-phenylethyl, 2-phenylethyl, 1-phenylpropyl, 2-phenylpropyl, 3-phenylpropyl, 4-phenylbutyl, 1-(1-naphthyl)ethyl, 1-(2-naphthyl)ethyl, 1-naphthylmethyl, 4-methylbenzyl, 4-isobutylbenzyl, 4-isopropylbenzyl, 4-tert-butylbenzyl, 4-methoxybenzyl, 3,4-dimethoxybenzyl, 3,4-methylenedioxybenzyl, 4-benzyloxybenzyl, 4-tert-butyldimethylsilyloxybenzyl, 4-nitrobenzyl, 4-fluorobenzyl, 4-chlorobenzyl, 4-bromobenzyl, 4-iodobenzyl, 4-cyanobenzyl, 4-dimethylaminobenzyl, 2-(4-methoxyphenyl)ethyl, 2-(4-benzyloxyphenyl)ethyl, 2-(4-tert-butyldimethylsilyloxyphenyl)ethyl, 2-(4-nitrophenyl)ethyl, etc.

An alkyl group represented by $R^4$ in the compound (1) may be a straight, branched or cyclic alkyl group, examples of which may include a straight, branched or cyclic alkyl group having 1 to 10 carbon atoms such as methyl, ethyl, propyl (including an isomer), butyl (including each isomer), pentyl (including each isomer), hexyl (including each isomer), heptyl (including each isomer), octyl (including each isomer), nonyl (including each isomer), decyl (including each isomer), cyclopropyl, cyclobutyl, cyclopentyl, cyclohexyl, cycloheptyl, cyclooctyl, cyclononyl and cyclodecyl groups. Preferably, they are straight, branched or cyclic alkyl groups having 1 to 6 carbon atoms, and more preferably, they are each group of methyl, ethyl, n-propyl, isopropyl, n-butyl, isobutyl, sec-butyl, tert-butyl, cyclopropyl, cyclobutyl, cyclopentyl and cyclohexyl.

An aryl group represented by $R^4$ in the compound (I) means either (15) an aryl group having no substituent or (16) an aryl group having one or more substituents.

As the above-mentioned (15) aryl group having no substituent, there are exemplified by each group of phenyl, naphthyl, anthracenyl, phenanthryl, etc. Among them, preferred is each group of phenyl and naphthyl, and more preferred is a phenyl group.

An aryl group of the above-mentioned (16) aryl group having one or more substituents means the same as defined for the aryl group of (15) the aryl group having no substituent. Preferred is each group of phenyl and naphthyl, and more preferred is a phenyl group.

As a substituent for (16) the aryl group having one or more substituents, there are exemplified by a straight or branched alkyl group having 1 to 6 carbon atoms such as methyl, ethyl, n-propyl, isopropyl, butyl (including each isomer), pentyl (including each isomer), hexyl (including each isomer) groups, etc.; each group of hydroxyl; nitro; cyano; halogen atom (fluorine, chlorine, bromine and iodine atoms); a straight or branched alkoxy group having 1 to 6 carbon atoms such as methoxy, ethoxy, propoxy (including each isomer), butoxy (including each isomer), pentyloxy (including each isomer), hexyloxy (including each isomer) groups, etc.; an amino group which may be substituted by a straight or branched alkyl group having 1 to 6 carbon atoms such as methyl, ethyl, propyl groups, etc.; an aralkyloxy group such as a benzyloxy group, etc.; a trimethylsilyloxy group; etc.

Preferred are an alkyl group having 1 to 6 carbon atoms, an alkoxy group having 1 to 6 carbon atoms, a halogen atom, each group of cyano, nitro, benzyloxy and trimethylsilyloxy, and more preferred is each group of methyl, ethyl, n-propyl, isopropyl, n-butyl, tert-butyl, methoxy, ethoxy, tert-butoxy, fluorine, chlorine and bromine atoms, and each group of nitro and benzyloxy. These substituents are not limited in numbers or positions and a plural number of substituents which may be the same or different may substitute.

An alkoxycarbonyl group represented by $R^4$ in the compound (1) may be a straight, branched or cyclic alkoxycarbonyl group having 1 to 6 carbon atoms, example of which may include each group of methoxycarbonyl, ethoxycarbonyl, n-propoxycarbonyl, isopropoxycarbonyl, n-butoxycarbonyl, sec-butoxycarbonyl, tert-butoxycarbonyl, n-pentyloxycarbonyl, n-hexyloxycarbonyl, cyclopropoxycarbonyl, cyclobutoxycarbonyl, cyclopentyloxycarbonyl, cyclohexyloxycarbonyl, etc. Preferably, they are each group of methoxycarbonyl, ethoxycarbonyl, n-propoxycarbonyl, isopropoxycarbonyl, n-butoxycarbonyl, sec-butoxycarbonyl, tert-butoxycarbonyl, cyclopropoxycarbonyl, cyclobutoxycarbonyl, cyclopentyloxycarbonyl and cyclohexyloxycarbonyl. More preferably, they are each group of methoxycarbonyl, ethoxycarbonyl, isopropoxycarbonyl, n-butoxycarbonyl, tert-butoxycarbonyl, and cyclohexyloxycarbonyl.

Specific examples of $R^4$ in the compound (I) may include each group of methyl, ethyl, n-propyl, isopropyl, n-butyl, isobutyl, sec-butyl, tert-butyl, n-hexyl, heptyl, octyl, nonyl, decyl, cyclopropyl, cyclobutyl, cyclopentyl, cyclohexyl, cycloheptyl, cyclooctyl, cyclononyl, cyclodecyl, phenyl, 1-naphthyl, 2-naphthyl, 2-methylphenyl, 3-methylphenyl, 4-methylphenyl, 4-benzyloxyphenyl, 3-benzyloxyphenyl, 2-benzyloxyphenyl, 4-trimethylsilyloxyphenyl, 4-nitrophenyl, 2-nitrophenyl, 3-nitrophenyl, 4-cyanophenyl, 3-cyanophenyl, 2-cyanophenyl, 4-fluorophenyl, 3-fluorophenyl, 2-fluorophenyl, 4-chlorophenyl, 3-chlorophenyl, 2-chlorophenyl, 4-bromophenyl, 2-bromophenyl, 4-iodophenyl, 4-methoxyphenyl, 3-methoxyphenyl, 2-methoxyphenyl, 3,4-dimethoxyphenyl, 4-ethoxyphenyl, 3-methoxy-4-ethoxyphenyl, 4-tert-butoxyphenyl, 3,4-methylenedioxyphenyl, 4-ethylphenyl, 4-n-propylphenyl, 4-isopropylphenyl, 4-tert-butylphenyl, 4-dimethylaminophenyl, 4-monomethylaminophenyl, 4-diethylamionophenyl, methoxycarbonyl, ethoxycarbonyl, n-propoxycarbonyl, isopropoxycarbonyl, n-butoxycarbonyl, sec-butoxycarbonyl, tert-butoxycarbonyl, n-pentyloxycarbonyl, n-hexyloxycarbonyl, cyclopropoxycarbonyl, cyclobutoxycarbonyl, cyclopentyloxycarbonyl, cyclohexyloxycarbonyl, cyano, etc.

Preferred examples may include each group of methyl, ethyl, n-propyl, isopropyl, n-butyl, isobutyl, sec-butyl, tert-butyl, n-hexyl, cyclohexyl, phenyl, 1-naphthyl, 2-naphthyl, methoxycarbonyl, ethoxycarbonyl, n-propoxycarbonyl, isopropoxycarbonyl, n-butoxycarbonyl, tert-butoxycarbonyl, cyclohexyloxycarbonyl and cyano. More preferred examples may include each group of methyl, ethyl, n-propyl, isopropyl, n-butyl, tert-butyl, phenyl, 1-naphthyl, 2-naphthyl, methoxycarbonyl, ethoxycarbonyl, tert-butoxycarbonyl and cyano.

Specific examples of the compound (I) represented by the formula (I) having the above-mentioned substituents $R^1$, $R^2$, $R^3$ and $R^4$ may include;

3-diphenylmethyl-7a-methoxy-6-methyl-4H-pyrano[3,2-d]-oxazol-2(3H)-one;

3-diphenylmethyl-7a-ethoxy-6-methyl-4H-pyrano[3,2-d]-oxazol-2(3H)-one;

3-diphenylmethyl-7a-isopropoxy-6-methyl-4H-pyrano[3,2-d]-oxazol-2(3H)-one;

3-diphenylmethyl-7a-((1)-menthyloxy)-6-methyl-4H-pyrano-[3,2-d]-oxazol-2(3H)-one;

3-diphenylmethyl-7a-phenoxy-6-methyl-4H-pyrano[3,2-d]-oxazol-2(3H)-one;

3-diphenylmethyl-7a-benzyloxy-6-methyl-4H-pyrano[3,2-d]-oxazol-2(3H)-one;

3-diphenylmethyl-7a-methoxy-6-ethyl-4H-pyrano[3,2-d]-oxazol-2(3H)-one;

3-diphenylmethyl-7a-methoxy-6-isopropyl-4H-pyrano[3,2-d]-oxazol-2(3H)-one;

3-diphenylmethyl-7a-methoxy-6-tert-butyl-4H-pyrano[3,2-d]-oxazol-2(3H)-one;

3-diphenylmethyl-7a-methoxy-6-methoxycarbonyl-4H-pyrano-[3,2-d]-oxazol-2(3H)-one;

3-diphenylmethyl-7a-methoxy-6-isopropoxycarbonyl-4H-pyrano-[3,2-d]-oxazol-2(3H)-one;

3-diphenylmethyl-7a-methoxy-6-ethoxycarbonyl-4H-pyrano[3,2-d]-oxazol-2(3H)-one;

3-diphenylmethyl-7a-methoxy-6-cyano-4H-pyrano[3,2-d]-oxazol-2(3H)-one;

3-diphenylmethyl-7a-methoxy-6-phenyl-4H-pyrano[3,2-d]-oxazol-2(3H)-one;

3-diphenylmethyl-7a-ethoxy-6-ethyl-4H-pyrano[3,2-d]-oxazol-2(3H)-one;

3-diphenylmethyl-7a-ethoxy-6-isopropyl-4H-pyrano[3,2-d]-oxazol-2(3H)-one;

3-diphenylmethyl-7a-ethoxy-6-tert-butyl-4H-pyrano[3,2-d]-oxazol-2(3H)-one;

3-diphenylmethyl-7a-ethoxy-6-isobutyl-4H-pyrano[3,2-d]-oxazol-2(3H)-one;

3-diphenylmethyl-7a-ethoxy-6-methoxycarbonyl-4H-pyrano[3,2-d]-oxazol-2(3H)-one;

3-diphenylmethyl-7a-ethoxy-6-phenyl-4H-pyrano[3,2-d]-oxazol-2(3H)-one;

3-diphenylmethyl-3a-methyl-7a-methoxy-6-methyl-4H-pyrano-[3,2-d]-oxazol-2(3H)-one;

3-diphenylmethyl-3a-phenyl-7a-methoxy-6-methyl-4H-pyrano-[3,2-d]-oxazol-2(3H)-one;

3-benzyl-7a-methoxy-6-methyl-4H-pyrano[3,2-d]-oxazol-2(3H)-one;

3-benzyl-7a-ethoxy-6-methyl-4H-pyrano[3,2-d]-oxazol-2(3H)-one;

3-benzyl-7a-isopropoxy-6-methyl-4H-pyrano[3,2-d]-oxazol-2(3H)-one;

3-benzyl-7a-phenoxy-6-methyl-4H-pyrano[3,2-d]-oxazol-2(3H)-one;

3-benzyl-7a-benzyloxy-6-methyl-4H-pyrano[3,2-d]-oxazol-2(3H)-one;

3-benzyl-7a-((1)-menthyloxy)-6-methyl-4H-pyrano[3,2-d]-oxazol-2(3H)-one;

3-benzyl-7a-methoxy-6-ethyl-4H-pyrano[3,2-d]-oxazol-2(3H)-one;

3-benzyl-7a-methoxy-6-isopropyl-4H-pyrano[3,2-d]-oxazol-2(3H)-one;
3-benzyl-7a-methoxy-6-n-butyl-4H-pyrano[3,2-d]-oxazol-2(3H)-one;
3-benzyl-7a-methoxy-6-tert-butyl-4H-pyrano[3,2-d]-oxazol-2(3H)-one;
3-benzyl-7a-methoxy-6-phenyl-4H-pyrano[3,2-d]-oxazol-2(3H)-one;
3-benzyl-3a-methyl-7a-methoxy-6-methyl-4H-pyrano[3,2-d]-oxazol-2(3H)-one;
3-benzyl-3a-phenylmethyl-7a-methoxy-6-methyl-4H-pyrano[3,2-d]-oxazol-2(3H)-one;
3-(1-phenylethyl)-7a-methoxy-6-methyl-4H-pyrano[3,2-d]-oxazol-2(3H)-one;
3-(1-phenylethyl)-7a-ethoxy-6-methyl-4H-pyrano[3,2-d]-oxazol-2(3H)-one;
3-(1-phenylethyl)-7a-isopropoxy-6-methyl-4H-pyrano[3,2-d]-oxazol-2(3H)-one;
3-(1-phenylethyl)-7a-methoxy-6-ethyl-4H-pyrano[3,2-d]-oxazol-2(3H)-one;
3-(1-phenylethyl)-7a-methoxy-6-propyl-4H-pyrano[3,2-d]-oxazol-2(3H)-one;
3-(1-phenylethyl)-7a-methoxy-6-n-butyl-4H-pyrano[3,2-d]-oxazol-2(3H)-one;
3-(1-phenylethyl)-7a-methoxy-6-tert-butyl-4H-pyrano[3,2-d]-oxazol-2(3H)-one;
3-(1-phenylethyl)-7a-methoxy-6-methoxycarbonyl-4H-pyrano-[3,2-d]-oxazol-2(3H)-one;
3-(1-phenylethyl)-7a-methoxy-6-cyano-4H-pyrano[3,2-d]-oxazol-2(3H)-one;
3-(1-phenylethyl)-7a-((1)-menthyloxy)-6-cyano-4H-pyrano-[3,2-d]-oxazol-2(3H)-one;
3-(1-phenylethyl)-3a-methyl-7a-methoxy-6-tert-butyl-4H-pyrano[3,2-d]-oxazol-2(3H)-one;
3-(1-phenylethyl)-7a-methoxy-6-phenyl-4H-pyrano[3,2-d]-oxazol-2(3H)-one;
3-(1-(1-naphthyl)ethyl)-7a-methoxy-6-methyl-4H-pyrano[3,2-d]-oxazol-2(3H)-one;
3-(1-(1-naphthyl)ethyl)-7a-ethoxy-6-methyl-4H-pyrano[3,2-d]-oxazol-2(3H)-one;
3-(1-(1-naphthyl)ethyl)-7a-isopropoxy-6-methyl-4H-pyrano-[3,2-d]-oxazol-2(3H)-one;
3-(1-(1-naphthyl)ethyl)-7a-methoxy-6-ethyl-4H-pyrano[3,2-d]-oxazol-2(3H)-one;
3-(1-(1-naphthyl)ethyl)-7a-methoxy-6-n-butyl-4H-pyrano[3,2-d]-oxazol-2(3H)-one;
3-(1-(1-naphthyl)ethyl)-7a-methoxy-6-hexyl-4H-pyrano[3,2-d]-oxazol-2(3H)-one;
3-(1-(1-naphthyl)ethyl)-7a-methoxy-6-methoxycarbonyl-4H-pyrano[3,2-d]-oxazol-2(3H)-one;
3-(1-(1-naphthyl)ethyl)-7a-methoxy-6-phenyl-4H-pyrano[3,2-d]-oxazol-2(3H)-one;
3-(1-(1-naphthyl)ethyl)-7a-methoxy-6-(3,4-dimethoxyphenyl)-4H-pyrano[3,2-d]-oxazol-2(3H)-one;
3-(1-(1-naphthyl)ethyl)-3a-methyl-7a-methoxy-6-methyl-4H-pyrano[3,2-d]-oxazol-2(3H)-one;
3-phenyl-7a-methoxy-6-methyl-4H-pyrano[3,2-d]-oxazol-2(3H)-one;
3-methyl-7a-methoxy-6-methyl-4H-pyrano[3,2-d]-oxazol-2(3H)-one;
3-(4-nitrobenzyl)-7a-methoxy-6-methyl-4H-pyrano[3,2-d]-oxazol-2(3H)-one;
3-(1-naphthyl)methyl-7a-isopropoxy-6-methyl-4H-pyrano[3,2-d]-oxazol-2(3H)-one;
3-(1-naphthyl)methyl-7a-methoxy-6-ethyl-4H-pyrano[3,2-d]-oxazol-2(3H)-one;
3-(1-naphthyl)methyl-7a-methoxy-6-tert-butyl-4H-pyrano[3,2-d]-oxazol-2(3H)-one;
3-(1-naphthyl)methyl-7a-methoxy-6-isopropyl-4H-pyrano[3,2-d]-oxazol-2(3H)-one;
3(1-(1-naphthyl)ethyl)-7a-methoxy-6-tert-butyl-4H-pyrano-[3,2-d]-oxazol-2(3H)-one;
3-diphenylmethyl-3a-methyl-7a-methoxy-6-n-butyl-4H-pyrano-[3,2-d]-oxazol-2(3H)-one; and
3-diphenylmethyl-7a-phenoxy-6-methyl-4H-pyrano[3,2-d]-oxazol-2(3H)-one.

Preferred examples may include;

3-diphenylmethyl-7a-methoxy-6-methyl-4H-pyrano[3,2-d]-oxazol-2(3H)-one;
3-diphenylmethyl-7a-ethoxy-6-methyl-4H-pyrano[3,2-d]-oxazol-2(3H)-one;
3-diphenylmethyl-7a-((1)-menthyloxy)-6-methyl-4H-pyrano-[3,2-d]-oxazol-2(3H)-one;
3-diphenylmethyl-3a-methyl-7a-methoxy-6-methyl-4H-pyrano-[3,2-d]-oxazol-2(3H)-one;
3-diphenylmethyl-7a-methoxy-6-ethyl-4H-pyrano[3,2-d]-oxazol-2(3H)-one;
3-diphenylmethyl-7a-methoxy-6-isopropyl-4H-pyrano[3,2-d]-oxazol-2(3H)-one;
3-diphenylmethyl-7a-methoxy-6-tert-butyl-4H-pyrano[3,2-d]-oxazol-2(3H)-one;
3-diphenylmethyl-7a-methoxy-6-methoxycarbonyl-4H-pyrano-[3,2-d]-oxazol-2(3H)-one;
3-diphenylmethyl-7a-methoxy-6-isopropoxycarbonyl-4H-pyrano-[3,2-d]-oxazol-2(3H)-one;
3-diphenylmethyl-7a-methoxy-6-ethoxycarbonyl-4H-pyrano[3,2-d]-oxazol-2(3H)-one;
3-diphenylmethyl-7a-methoxy-6-cyano-4H-pyrano[3,2-d]-oxazol-2(3H)-one;
3-diphenylmethyl-7a-methoxy-6-phenyl-4H-pyrano[3,2-d]-oxazol-2(3H)-one;
3-diphenylmethyl-7a-ethoxy-6-ethyl-4H-pyrano[3,2-d]-oxazol-2(3H)-one;
3-diphenylmethyl-7a-ethoxy-6-isopropyl-4H-pyrano[3,2-d]-oxazol-2(3H)-one;
3-diphenylmethyl-7a-ethoxy-6-tert-butyl-4H-pyrano[3,2-d]-oxazol-2(3H)-one;
3-diphenylmethyl-7a-ethoxy-6-isobutyl-4H-pyrano[3,2-d]-oxazol-2(3H)-one;
3-diphenylmethyl-7a-ethoxy-6-methoxycarbonyl-4H-pyrano[3,2-d]-oxazol-2(3H)-one;
3-diphenylmethyl-7a-ethoxy-6-phenyl-4H-pyrano[3,2-d]-oxazol-2(3H)-one;
3-(1-phenylethyl)-7a-methoxy-6-methyl-4H-pyrano[3,2-d]-oxazol-2(3H)-one;
3-(1-phenylethyl)-7a-isopropoxy-6-methyl-4H-pyrano[3,2-d]-oxazol-2(3H)-one;
3-(1-phenylethyl)-7a-((1)-menthyloxy)-6-methyl-4H-pyrano-[3,2-d]-oxazol-2(3H)-one;
3-(1-phenylethyl)-7a-methoxy-6-ethyl-4H-pyrano[3,2-d]-oxazol-2(3H)-one;
3-(1-phenylethyl)-7a-methoxy-6-(n-butyl)-4H-pyrano[3,2-d]-oxazol-2(3H)-one;
3-benzyl-7a-methoxy-6-methyl-4H-pyrano[3,2-d]-oxazol-2(3H)-one;
3-benzyl-7a-isopropoxy-6-methyl-4H-pyrano[3,2-d]-oxazol-2(3H)-one;
3-benzyl-7a-((1)-menthyloxy)-6-methyl-4H-pyrano[3,2-d]-oxazol-2(3H)-one;
3-benzyl-7a-methoxy-6-tert-butyl-4H-pyrano[3,2-d]-oxazol-2(3H)-one;
3-benzyl-7a-methoxy-6-ethyl-4H-pyrano[3,2-d]-oxazol-2(3H)-one;
3-benzyl-7a-methoxy-6-isopropyl-4H-pyrano[3,2-d]-oxazol-2(3H)-one;

3-benzyl-7a-methoxy-6-methoxycarbonyl-4H-pyrano[3,2-d]-oxazol-2(3H)-one;
3-benzyl-7a-methoxy-6-phenyl-4H-pyrano[3,2-d]-oxazol-2(3H)-one;
3-(1-naphthyl)methyl-7a-isopropoxy-6-methyl-4H-pyrano[3,2-d]-oxazol-2(3H)-one;
3-(1-naphthyl)methyl-7a-methoxy-6-ethyl-4H-pyrano[3,2-d]-oxazol-2(3H)-one;
3-(1-naphthyl)methyl-7a-methoxy-6-tert-butyl-4H-pyrano[3,2-d]-oxazol-2(3H)-one;
3-(1-naphthyl)methyl-7a-methoxy-6-isopropyl-4H-pyrano[3,2-d]-oxazol-2(3H)-one;
3-(1-(1-naphthyl)ethyl)-7a-methoxy-6-methyl-4H-pyrano[3,2-d]-oxazol-2(3H)-one; and
3-(1-(1-naphthyl)ethyl)-7a-methoxy-6-tert-butyl-4H-pyrano-[3,2-d]-oxazol-2(3H)-one.

More preferred examples may include;
3-diphenylmethyl-7a-methoxy-6-methyl-4H-pyrano[3,2-d]-oxazol-2(3H)-one;
3-(1-phenylethyl)-7a-methoxy-6-methyl-4H-pyrano[3,2-d]-oxazol-2(3H)-one; and
3-(1-(1-naphthyl)ethyl)-7a-methoxy-6-methyl-4H-pyrano[3,2-d]-oxazol-2(3H)-one.

The 7a-alkoxy-4H-pyrano[3,2-d]-oxazol-2(3H)-one of the present invention represented by the formula (I) can be prepared, as shown by the formula (V), by reacting a 5-alkoxy-2(3H)-oxazolone represented by the formula (II) with an α, β-unsaturated ketone represented by the formula (III) in an organic solvent in the presence of a Lewis acid represented by the formula (IV).

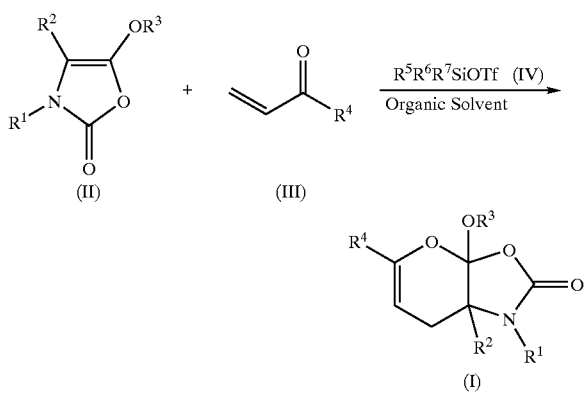

wherein $R^1$, $R^2$, $R^3$ and $R^4$ have the same meanings as defined above, $R^5$, $R^6$ and $R^7$ each independently represent an alkyl group having 1 to 6 carbon atoms and Tf represents a trifluoromethanesulfonyl group.

The 5-alkoxy-2(3H)-oxazolones to be used in the reaction of the present invention are represented by the formula (II). In the formula (II), $R^1$, $R^2$ and $R^3$ are the same as defined above.

Specific examples of the above 5-alkoxy-2(3H)-oxazolones may include;
3-benzyl-5-methoxy-2(3H)-oxazolone;
3-benzyl-5-ethoxy-2(3H)-oxazolone;
3-benzyl-5-n-propyloxy-2(3H)-oxazolone;
3-benzyl-5-n-butyloxy-2(3H)-oxazolone;
3-benzyl-5-isopropyloxy-2(3H)-oxazolone;
3-benzyl-5-phenyloxy-2(3H)-oxazolone;
3-benzyl-5-(4-nitrophenyloxy)-2(3H)-oxazolone;
3-benzyl-5-benzyloxy-2(3H)-oxazolone;
3-benzyl-5-menthyloxy-2(3H)-oxazolone;
3-benzyl-5-(8-phenylmenthyloxy)-2(3H)-oxazolone;
3-benzyl-4-methyl-5-methoxy-2(3H)-oxazolone;
3-benzyl-4-phenylmethyl-5-methoxy-2(3H)-oxazolone;
3-diphenylmethyl-5-methoxy-2(3H)-oxazolone;
3-diphenylmethyl-5-ethoxy-2(3H)-oxazolone;
3-diphenylmethyl-5-n-propyloxy-2(3H)-oxazolone;
3-diphenylmethyl-5-n-butyloxy-2(3H)-oxazolone;
3-diphenylmethyl-5-isopropyloxy-2(3H)-oxazolone;
3-diphenylmethyl-5-phenyloxy-2(3H)-oxazolone;
3-diphenylmethyl-5-benzyloxy-2(3H)-oxazolone;
3-diphenylmethyl-5-menthyloxy-2(3H)-oxazolone;
3-diphenylmethyl-5-(8-phenylmenthyloxy)-2(3H)-oxazolone;
3-diphenylmethyl-4-methyl-5-methoxy-2(3H)-oxazolone;
3-diphenylmethyl-4-benzyloxyphenylmethyl-5-methoxy-2(3H)-oxazolone;
3-diphenylmethyl-4-phenyl-5-methoxy-2(3H)-oxazolone;
3-(1-phenylethyl)-5-methoxy-2(3H)-oxazolone;
3-(1-phenylethyl)-5-ethoxy-2(3H)-oxazolone;
3-(1-phenylethyl)-5-n-propyloxy-2(3H)-oxazolone;
3-(1-phenylethyl)-5-n-butyl oxy-2(3H)-oxazolone;
3-(1-phenylethyl)-5-isopropyloxy-2(3H)-oxazolone;
3-(1-phenylethyl)-5-phenyloxy-2(3H)-oxazolone;
3-(1-phenylethyl)-5-(4-nitrophenyl)oxy-2(3H)-oxazolone;
3-(1-phenylethyl)-5-benzyloxy-2(3H)-oxazolone;
3-(1-phenylethyl)-5-menthyloxy-2(3H)-oxazolone;
3-(1-phenylethyl)-5-(8-phenylmenthyloxy)-2(3H)-oxazolone;
3-(1-phenylethyl)-4-methyl-5-methoxy-2(3H)-oxazolone;
3-(1-phenylethyl)-4-phenylmethyl-5-methoxy-2(3H)-oxazolone;
3-(1-phenylethyl)-4-(2-phenylethyl)-5-methoxy-2(3H)-oxazol-one;
3-(1-(1-naphthyl)ethyl)-5-methoxy-2(3H)-oxazolone;
3-(1-(1-naphthyl)ethyl-5-ethoxy-2(3H)-oxazolone;
3-(1-(1-naphthyl)ethyl-5-isopropyloxy-2(3H)-oxazolone;
3-(1-(1-naphthyl)ethyl-5-phenyloxy-2(3H)-oxazolone;
3-(1-(1-naphthyl)ethyl-5-benzyloxy-2(3H)-oxazolone;
3-(1-(1-naphthyl)ethyl-5-menthyloxy-2(3H)-oxazolone;
3-(1-(1-naphthyl)ethyl-5-(8-phenylmenthyloxy)-2(3H)-oxazol-one;
3-(1-(1-naphthyl)ethyl)-4-methyl-5-methoxy-2(3H)-oxazolone;
3-(1-phenylethyl)-4-phenylmethyl-5-methoxy-2(3H)-oxazolone;
3-phenyl-5-methoxy-2(3H)-oxazolone;
3-phenyl-4-methyl-5-methoxy-2(3H)-oxazolone;
3-phenyl-4-phenylmethyl-5-methoxy-2(3H)-oxazolone;
3-(2-methoxyphenyl)-5-methoxy-2(3H)-oxazolone;
3-(3-methoxyphenyl)-5-methoxy-2(3H)-oxazolone;
3-(4-methoxyphenyl)-5-methoxy-2(3H)-oxazolone;
3-methyl-5-methoxy-2(3H)-oxazolone;
3-methyl-5-benzyloxy-2(3H)-oxazolone;
3-methyl-4-methyl-5-methoxy-2(3H)-oxazolone; etc.

The α,β-unsaturated ketone to be used in the reaction of the present invention is represented by the formula (III). In the formula (III), $R^4$ is the same as defined above.

Specific examples of the above α,β-unsaturated ketones may include;
3-oxo-1-butene;
3-oxo-1-pentene;
3-oxo-1-hexene;
3-oxo-1-heptene;
3-oxo-1-octene;
3-oxo-1-nonene;
3-oxo-1-decene;
3-oxo-4-methyl-1-pentene;

3-oxo-5-methyl-1-hexene;
3-oxo-4-phenyl-1-butene;
3-oxo-4-dimethyl-1-pentene;
3-oxo-3-phenyl-1-propene;
3-oxo-3-(2-naphthyl)-1-propene;
3-oxo-4-(2-furyl)-1-butene;
3-oxo-5-methyl-1-heptene;
3-oxo-5-ethyl-1-heptene;
3-oxo-5-methyl-1-octene;
3-oxo-4,4-diethyl-1-hexene;
3-oxo-7-methyl-1-octene;
3-oxo-5,5-dimethyl-1-hexene;
3-oxo-3-(4-methylphenyl)-1-butene;
3-oxo-3-(4-ethylphenyl)-1-butene;
3-oxo-3-(4-bromophenyl)-1-butene;
3-oxo-3-(4-chlorophenyl)-1-butene;
3-oxo-3-(4-benzylphenyl)-1-butene;
3-oxo-3-(4-dimethylaminophenyl)-1-butene;
3-oxo-3-(4-methoxyphenyl)-1-butene;
3-oxo-3-(2,4-dimethoxylphenyl)-1-butene;
3-oxo-3-(3,4-dimethoxylphenyl)-1-butene;
3-oxo-3-(2-nitrophenyl)-1-butene;
3-oxo-3-(2-acetoxyphenyl)-1-butene;
3-oxo-3-(2-phenanthryl)-1-butene;
3-oxo-3-methoxycarbonyl-1-butene;
3-oxo-3-ethoxycarbonyl-1-butene;
3-oxo-3-isopropoxycarbonyl-1-butene;
3-oxo-3-tert-butoxycarbonyl-1-butene;
3-oxo-3-benzyloxycarbonyl-1-butene;
3-oxo-3-cyano-1-butene; etc.

An amount of the above α,β-unsaturated ketone to be used is preferably 1.0 to 10.0 mol, more preferably 1.0 to 5.0 mol based on 1 mol of the 5-alkoxy-2(3H)-oxazolone.

The Lewis acid to be used in the reaction in the present invention is represented by the formula (IV). In the formula (IV), the alkyl group having 1 to 6 carbon atoms represented by $R^5$, $R^6$ and $R^7$ is a straight, branched or cyclic alkyl group having 1 to 6 carbon atoms, examples of which may include each group of methyl, ethyl, propyl (including an isomer), butyl (including each isomer), pentyl (including each isomer) and hexyl (including each isomer). Preferably, they are each group of methyl, ethyl, n-propyl, isopropyl, n-butyl, isobutyl, sec-butyl and tert-butyl.

Examples of the above Lewis acid may include;
trimethylsilyltriflate;
triethylsilyltriflate;
tri(n-propyl)silyltriflate;
tert-butyldimethylsilyltriflate;
triisopropylsilyltriflate; etc.

An amount of the above-mentioned Lewis acid to be used is preferably 0.001 to 2.0 mol, more preferably 0.005 to 0.5 mol based on 1 mol of the 5-alkoxy-2(3H)-oxazolone.

The organic solvent to be used in the present invention is not limited as long as it is not involved in a reaction. For example, halogenated aliphatic hydrocarbons such as chlorobenzene, dichlorobenzene, methylene chloride, chloroform, carbon tetrachloride, 1,2-dichloroethane, etc.; aromatic hydrocarbons such as benzene, toluene, xylene, etc.; ethers such as diethyl ether, diisopropyl ether, dibutyl ether, dimethoxyethane, tetrahydrofuran, dioxane, etc.; and nitriles such as acetonitrile, propionitrile, benzonitrile, etc. Preferably, they are halogenated hydrocarbons and more preferably, they are methylene chloride and/or 1,2-dichloroethane.

Though an amount of the above-mentioned organic solvent to be used may be properly adjusted according to uniformity of the solution or stirring property of the same, it is preferably 0.5 to 100 liters, more preferably, 1 to 30 liters based on 1 mol of the 5-alkoxy-2(3H)-oxazolone.

The reaction according to the present invention may be carried out, for example, by mixing a 5-alkoxy-2(3H)-oxazolone, an α,β-unsaturated ketone, a Lewis acid, and an organic solvent in an inert gas atmosphere, and letting the reaction undergo preferably at −80 to 200° C., and more preferably at −78 to 30° C., etc. There is no restriction on a reaction pressure during the reaction.

The 7a-alkoxy-4H-pyrano[3,2-d]-oxazol-2(3H)-one obtainable in the present invention is separated and purified, after completion of the reaction, according to the conventional method such as recrystallization, distillation, column chromatography, etc.

EXAMPLES

In the following, the present invention is explained in more detail by referring to Examples, but the present invention is not limited by these Examples.

Example 1

To a 50 ml glass flask equipped with a stirrer, a thermometer and a dropping funnel were added 140.7 mg (0.50 mmol) of 3-diphenylmethyl-5-methoxy-2(3H)-oxazolone and 3.0 ml of methylene chloride and the mixture was cooled down to −78° C. under nitrogen atmosphere. Subsequently, 52.6 mg (0.75 mmol) of methyl vinyl ketone and 9.1 μl (0.05 mmol) of trimethylsilyltriflate were added thereto and a reaction was carried out for 2 hours at the same temperature. After completion of the reaction, 15 ml of an aqueous solution of saturated sodium hydrogen carbonate was added thereto and the mixture was extracted with 15 ml of methylene chloride. After separating the organic layer (methylene chloride layer), it was washed twice with each 15 ml of water, and then, it was dried over anhydrous magnesium sulfate. It was then subjected to filtration and the resultant filtrate was concentrated under reduced pressure to give 200 mg of an oily product. This was purified by a silica gel column chromatography (eluent: n-hexane/ethyl acetate=20/1 (volume ratio)), to obtain 158.4 mg of 3-diphenylmethyl-7a-methoxy-6-methyl-4H-pyrano[3,2-d]-oxazol-2(3H)-one as white crystal (isolation yield: 90%; based on 3-diphenylmethyl-5-methoxy-2(3H)-oxazolone).

The 3-diphenylmethyl-7a-methoxy-6-methyl-4H-pyrano[3,2-d]-oxazol-2(3H)-one is a novel compound having physical properties shown below.

$^1$H-NMR (δ(ppm), $CDCl_3$): 1.80 (m, 2H), 1.86 (s, 3H), 3.59 (s, 3H), 3.73–3.75 (m, 1H), 4.81–4.84 (m, 1H), 6.27 (s, 1H), 7.25–7.40 (m, 10H).

$^{13}$C-NMR (δ(ppm), $CDCl_3$): 19.1, 23.5, 50.5, 51.1, 59.8, 99.9, 115.9, 127.8, 128.1, 128.2, 128.5, 128.7, 128.8, 137.6, 138.6, 150.8, 155.2.

MS (CI, i-$C_4H_{10}$) m/z: 352 (MH$^+$).

Elemental analysis (%): Calcd: C;72.58, H;5.37, N;4.98, Found: C;72.45, H;5.40, N;4.98.

Example 2

To a 50 ml glass flask equipped with a stirrer, a thermometer and a dropping funnel were added 134.7 mg (0.50 mmol) of 3-(R)-(1-(1-naphthyl)ethyl)-5-methoxy-2(3H)-oxazolone and 3.0 ml of methylene chloride and the mixture was cooled down to −78° C. under nitrogen atmosphere. Subsequently, 52.6 mg (0.75 mmol) of methyl vinyl ketone and 9.1 μl (0.05 mmol) of trimethylsilyltriflate were added thereto and a reaction was carried out for one hour at the same temperature. After completion of the reaction, 15 ml of an aqueous solution of saturated sodium hydrogen carbonate was added thereto and the mixture was extracted with 15 ml of methylene chloride. After separating the organic layer (methylene chloride layer), it was washed twice with each 15 ml of water, and dried over anhydrous magnesium sulfate. It was then subjected to filtration and the resultant filtrate was concentrated under reduced pressure to give 181 mg of diastereomer mixture of 3-(R)-(1-(1-naphthyl)-ethyl)-7a-methoxy-6-methyl-4H-pyrano[3,2-d]-oxazol-2(3H)-one as an oily product (formation ratio between diastereomers was 66:34 (analyzed value from high performance liquid chromatography)). This was purified by a silica gel column chromatography (eluent: n-hexane/ethyl acetate=20/1 (volume ratio)), to obtain 76 mg of a major diastereomer as white crystal (isolation yield: 45%; based on 3-(R)-(1-(1-naphthyl)ethyl)-5-methoxy-2(3H)-oxazolone).

The major diastereomer of 3-(R)-(1-(1-naphthyl)ethyl)-7a-methoxy-6-methyl-4H-pyrano[3,2-d]-oxazol-2(3H)-one is a novel compound having physical properties shown below.

$^1$H-NMR (δ(ppm), CDCl$_3$): 0.72–0.79 (m, 1H), 1.23–1.31 (m, 1H), 1.67 (d, J=1.0 Hz, 3H), 1.76 (d, J=6.8 Hz, 3H), 3.57 (s, 3H), 3.80 (dd, J=5.3 Hz, J=4.4 Hz, 1H), 3.94–3.98 (m, 1H), 5.99 (q, J=6.8 Hz, 1H), 7.42–7.59 (m, 4H), 7.85 (t, J=8.3 Hz, 2H), 8.18 (d, J=8.3 Hz, 1H).

$^{13}$C-NMR (δ(ppm), CDCl$_3$): 16.0, 18.8, 48.1, 50.4, 58.2, 100.5, 116.2, 123.8, 124.9, 126.2, 126.8, 128.6, 129.2, 131.9, 133.6, 135.0, 150.2, 155.1.

MS (CI, i-C$_4$H$_{10}$) m/z: 340 (MH$^+$), 155.

IR (KBr method, cm$^{-1}$): 1749.7.

Elemental analysis (%): calcd: C;70.78, H;6.24, N:4.13, Found: C;70.79, H;6.25, N:4.18.

Example 3

To a 50 ml glass flask equipped with a stirrer, a thermometer and a dropping funnel were added 134.7 mg (0.50 mmol) of 3-(R)-(1-phenylethyl)-5-methoxy-2(3H)-oxazolone and 3.0 ml of methylene chloride and the mixture was cooled down to −78° C. under nitrogen atmosphere. Subsequently, 52.6 mg (0.75 mmol) of methyl vinyl ketone and 9.1 μl (0.05 mmol) of trimethylsilyltriflate were added thereto and a reaction was carried out for one hour at the same temperature. After completion of the reaction, 15 ml of an aqueous solution of saturated sodium hydrogen carbonate was added thereto and the mixture was extracted with 15 ml of methylene chloride. After separating the organic layer (methylene chloride layer), it was washed twice with each 15 ml of water, and dried over anhydrous magnesium sulfate. It was then subjected to filtration and the resultant filtrate was concentrated under reduced pressure to give an oily product. This was purified by a silica gel column chromatography (eluent: n-hexane/ethyl acetate=20/1 (volume ratio)), to obtain 114 mg of diastereomer mixture of 3-(R)-(1-phenylethyl)-7a-methoxy-6-methyl-4H-pyrano[3,2-d]-oxazol-2(3H)-one as a colorless transparent oily product (isolation yield: 67%; based on 3-(R)-(1-phenylethyl)-5-methoxy-2(3H)-oxazolone; formation ratio between diastereomers was 65:35 (analyzed value from high performance liquid chromatography)).

The diastereomer mixture of 3-(R)-(1-phenylethyl)-7a-methoxy-6-methyl-4H-pyrano[3,2-d]-oxazol-2(3H)-one is a novel compound having physical properties shown below.

$^1$H-NMR (δ(ppm), CDCl$_3$).

major isomer: 1.52–1.61 (m, 2H), 1.23–1.31 (m, 1H), 1.67 (d, J=7.3 Hz, 3H), 1.78 (s, 3H), 3.59 (s, 3H), 3.56 (t, J=4.8 Hz, 1H), 3.92 (dd, J=3.4 Hz, J=5.4 Hz, 1H), 5.17 (q, J=6.8 Hz, 1H), 7.23–7.43 (m, 5H), minor isomer: 1.65 (d, J=7.3 Hz, 3H), 1.82 (s, 3H), 3.83–3.90 (m. 2H), 3.54 (s, 3H), 4.51–4.55 (m, 1H), 4.89 (t, J=5.4 Hz, 1H), 5.10 (q, J=7.3 Hz, 1H), 7.23–7.43 (m, 5H).

MS(CI, i-C$_4$H$_{10}$) m/z: 290 (MH$^+$), 105.

Reference Example 1
Synthesis of Trifluoroacetate of 5-methylproline Methyl Ester To a 50 ml glass flask equipped with a stirrer, a thermometer and a dropping funnel were added 932.6 mg (2.65 mmol) of 3-diphenylmethyl-7a-methoxy-6-methyl-4H-pyrano[3,2-d]-oxazol-2(3H)-one synthesized in the same manner as in Example 1, 906.5 mg (7.95 mmol) of trifluoro acetate and 26 ml of methylene chloride, and the mixture was reacted under argon atmosphere at room temperature for 17 hours. Subsequently, 26 ml of methanol and 564 mg of 5% by weight Pd/C were added thereto and reaction was carried out under hydrogen gas atmosphere (under normal pressure) at room temperature for 16 hours. After completion of the reaction, the reaction mixture was filtrated and the resultant filtrate was concentrated under reduced pressure to give 1228 mg of colorless transparent oily product. This was washed with each 20 ml of diethyl ether for 3 times, with each 20 ml of n-hexane for 2 times and with 20 ml of diethyl ether for once in this order, and dried under reduced pressure to give 534 mg of trifluoroacetate of 5-methylproline methyl ester as white crystal (isolation yield: 78%; based on 3-diphenylmethyl-7a-methoxy-6-methyl-4H-pyrano[3,2-d]-oxazol-2(3H)-one).

Physical properties of the trifluoroacetate of 5-methylproline methyl ester are shown below.

$^1$H-NMR (δ(ppm), CDCl$_3$): 1.51 (d, J=6.4 Hz, 3H), 1.61–1.72 (m, 1H), 2.19–2.32 (m, 2H), 2.40–2.52 (m, 1H), 3.85 (s, 3H), 3.85–3.94 (m, 1H), 4.53 (dd, J=9.3 Hz, J=4.9 Hz, 1H), $^{13}$C-NMR (δ(ppm), CDCl$_3$): 17.7, 28.4, 31.4, 53.7, 56.8, 59.0, 170.3.

MS (CI, i-C$_4$H$_{10}$) m/z: 144 (MH$^+$), 84.

Elemental analysis(%): Calcd: C;42.03, H;5.49, N:5.42, Found: C;41.74, H;5.48, N:5.44.

According to the present invention, there are provided a novel 7a-alkoxy-4H-pyrano[3,2-d]-oxazol-2(3H)-one that can be used as a starting material for synthesizing a pharmaceutical product, an agricultural chemical and other fine chemical products, and a process for producing the same.

What is claimed is:

1. A 7a-alkoxy-4H-pyrano[3,2-d]-oxazol-2(3H)-one represented by the formula (I):

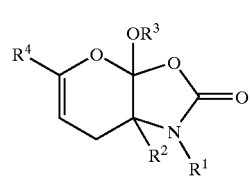

wherein R$^1$ represents a hydrogen atom, an alkyl group, an alkenyl group, an aryl group or an aralkyl group; R$^2$ represents a hydrogen atom; R$^3$ is a methyl group; and R$^4$ represents a methyl group.

2. The 7a-alkoxy-4H-pyrano[3,2-d]-oxazol-2(3H)-one according to claim 1, wherein R$^1$ represents an alkyl group, a phenyl group or an aralkyl group, R$^2$ represents a hydrogen atom, R$^3$ is a methyl group, and R$^4$ represents a methyl group.

3. The 7a-alkoxy-4H-pyrano[3,2-d]-oxazol-2(3H)-one according to claim 1, wherein $R^1$ represents a benzyl group, a 1-phenylethyl group, a diphenylmethyl group, a phenyl group, a (1-naphthyl)methyl group or a 1-(1-naphthyl)ethyl group, $R^2$ represents a hydrogen atom, $R^4$ represents a methyl group.

4. The 7a-alkoxy-4H-pyrano[3,2-d]-oxazol-2(3H)-one according to claim 1, wherein the 7a-alkoxy-4H-pyrano[3,2-d]-oxazol-2(3H)-one represented by the formula (I) is at least one compound selected from the group consisting of:

3-diphenylmethyl-7a-ethoxy-6-methyl-4H-pyrano[3,2-d]-oxazol-2(3H)-one;

3-diphenylmethyl-7a-methoxy-6-methyl-4H-pyrano[3,2-d]-oxazol-2(3H)-one;

3-diphenylmethyl-3a-methyl-7a-methoxy-6-methyl-4H-pyrano[3,2-d]-oxazol-2(3H)-one;

3-(1-phenylethyl)-7a-methoxy-6-methyl-4H-pyrano[3,2-d]-oxazol-2(3H)-one;

3-benzyl-7a-methoxy-6-methyl-4H-pyrano[3,2-d]-oxazol-2(3H)-one;

3-(1-(1-naphthyl)ethyl)-7a-methoxy-6-methyl-4H-pyrano[3,2-d]-oxazol-2(3H)-one.

5. A process for producing a 7a-alkoxy-4H-pyrano[3,2-d]-oxazol-2(3H)-one represented by the formula (I):

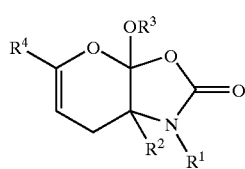
(I)

wherein $R^1$ represents a hydrogen atom, an alkyl group, an alkenyl group, an aryl group or an aralkyl group; $R^2$ represents a hydrogen atom; $R^3$ represents a methyl group; and $R^4$ represents a methyl group, which comprises reacting a 5-alkoxy-2(3H)-oxazolone represented by the formula (II):

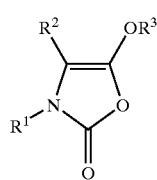
(II)

wherein $R^1$, $R^2$ and $R^3$ are the same as defined above, with an α, β-unsaturated ketone represented by the formula (III):

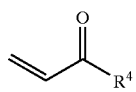
(III)

wherein $R^4$ is the same as defined above, in an organic solvent in the presence of a Lewis acid.

6. The process for producing a 7a-alkoxy-4H-pyrano[3,2-d]-oxazol-2(3H)-one according to claim 5, wherein the Lewis acid is represented by the formula (IV):

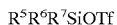
$R^5R^6R^7SiOTf$ (IV)

wherein $R^5$, $R^6$ and $R^7$ each independently represent an alkyl group having 1 to 6 carbon atoms and Tf represents a trifluoromethanesulfonyl group.

7. The 7a-alkoxy-4H-pyrano[3,2-d]-oxazol-2(3H)-one according to claim 1, wherein $R^1$ is an alkyl group, an aralkyl group or a phenyl group, $R^2$ is a hydrogen atom, $R^3$ is a methyl group, and R4 is a methyl group.

8. The 7a-alkoxy-4H-pyrano[3,2-d]-oxazol-2(3H)-one according to claim 1, wherein $R^1$ is an alkyl group having 1 to 6 carbon atoms, an aralkyl group or a phenyl group, $R^2$ is a hydrogen atom, $R^3$ is a methyl group, and $R^4$ is a methyl group.

9. 3-diphenylmethyl-7a-methoxy-6-methyl-4H-pyrano[3,2-d]oxazol-2(3H)-one.

* * * * *